(12) United States Patent
Kim et al.

(10) Patent No.: US 9,269,240 B2
(45) Date of Patent: Feb. 23, 2016

(54) CASTER INDICATOR

(71) Applicant: SAMSUNG MEDISON CO., LTD., Gangwon-Do (KR)

(72) Inventors: Seung Tae Kim, Seoul (KR); Soon Deok Kim, Gyeonggi-do (KR); Jung Sik Song, Seoul (KR)

(73) Assignee: Samsung Medison Co., Ltd., Gangwon-do (KR)

( * ) Notice: Subject to any disclaimer, the term of this patent is extended or adjusted under 35 U.S.C. 154(b) by 348 days.

(21) Appl. No.: 13/750,705

(22) Filed: Jan. 25, 2013

(65) Prior Publication Data

US 2013/0194072 A1    Aug. 1, 2013

(30) Foreign Application Priority Data

Jan. 26, 2012   (KR) .................. 10-2012-0007565

(51) Int. Cl.
*G08B 5/36* (2006.01)
*B60B 33/02* (2006.01)
(Continued)

(52) U.S. Cl.
CPC ............... *G08B 5/36* (2013.01); *A61B 8/4405* (2013.01); *B60B 33/021* (2013.01); *B60B 33/026* (2013.01); *B60B 33/0039* (2013.01); *B60B 33/0049* (2013.01); *B60B 33/0057* (2013.01); *B60B 33/0068* (2013.01); *B60B 33/0073* (2013.01); *B60B 2900/3312* (2013.01); *B60B 2900/531* (2013.01)

(58) Field of Classification Search
CPC   B60B 33/0002; B60B 33/00; B60B 33/0044; B60B 33/02; B60B 33/0068; B60B 33/021; B60B 33/0042; A61G 7/1046

USPC ........ 340/1.1, 6.1; 188/1.12; 5/86.1; 16/18 R, 16/35 R, 42 R, 42 T
See application file for complete search history.

(56) References Cited

U.S. PATENT DOCUMENTS 4,998,320 A     3/1991  Lange
5,450,639 A *   9/1995  Weismiller ............... A61G 7/00
                                                       16/35 R
(Continued)

FOREIGN PATENT DOCUMENTS

DE    3837307 C1    11/1989
DE    10105614 A1    7/2002
EP    1329208 A2    7/2003
(Continued)

OTHER PUBLICATIONS

Korean Office Action issued in Korean Patent Application No. 10-2012-0007565 dated Jun. 27, 2013.
(Continued)

*Primary Examiner* — Brian Zimmerman
*Assistant Examiner* — An T Nguyen
(74) *Attorney, Agent, or Firm* — McDermott Emery & Will LLP

(57) ABSTRACT

A caster indicator displays the state of casters provided on an ultrasonic diagnostic apparatus or a medical bed. The caster indicator includes a position sensing unit sensing the position of levers determining the state of casters, and a display unit displaying the state of the casters according to the position of the levers. With the caster indicator, a user easily confirms the state of the casters, even if a medical electronic apparatus, such as the ultrasonic diagnostic apparatus or the medical bed, is located at a dark place.

16 Claims, 9 Drawing Sheets

(51) Int. Cl.
*A61B 8/00* (2006.01)
*B60B 33/00* (2006.01)

(56) References Cited

U.S. PATENT DOCUMENTS

2003/0132065 A1 7/2003 Suzuki
2004/0117943 A1* 6/2004 Block et al. .................. 16/18 R

FOREIGN PATENT DOCUMENTS

| EP | 1329208 | A3 | 7/2003 |
| GB | 2245163 | A * | 1/1992 |
| KR | 1020100056785 | A | 5/2010 |
| WO | 03088885 | A1 | 10/2003 |
| WO | WO 03088885 | A1 * | 10/2003 |

OTHER PUBLICATIONS

Extended European Search Report issued in Application No. 13152637.8 dated May 23, 2013.

European Office Action dated Apr. 9, 2015 issued in corresponding European Patent Application No. 13152637.8.

* cited by examiner

CASTER INDICATOR

CROSS-REFERENCE TO RELATED APPLICATION

This application claims the benefit of Korean Patent Application No. 10-2012-0007565, filed on Jan. 26, 2012 in the Korean Intellectual Property Office, the disclosure of which is incorporated herein by reference.

TECHNICAL FIELD

Embodiments of the present disclosure relate to a caster indicator which displays the state of casters.

BACKGROUND

Medical electronic apparatuses, such as an ultrasonic diagnostic apparatus, are provided with a plurality of casters for mobility. In general, a medical electronic apparatus is provided with three or more casters. One example of the medical electronic apparatuses uses a mechanism which may control two or more casters at the same time using a link.

However, in such a medical electronic apparatus, in order to confirm the operating state of the casters, a user often needs to directly move the apparatus, or to directly look the casters or to confirm the states of the mechanism used in the apparatus and parts of the mechanism, thus experiencing inconvenience.

SUMMARY

Therefore, one aspect of the present disclosure is to provide a caster indicator which displays the state of casters.

Additional aspects of the present subject matter will be set forth in part in the description which follows and, in part, will be obvious from the description, or may be learned by practice of the disclosed subject matter.

In accordance with one aspect of the present disclosure, a caster indicator includes a lever configured to determine the state of the caster and a display unit displaying the state of the caster according to the position of the lever.

The caster indicator may further include a position sensing unit sensing the position of the lever.

In some embodiments, indicators corresponding to respective states of the caster according to the sensed position of the lever may be displayed on the display unit.

In some embodiments, the display unit may be divided into plural regions, and indicators (including marks, etc.) corresponding to respective states of the caster may be displayed in the respective regions.

In some embodiments, among the indicators displayed in the respective regions, the indicator corresponding to the state of the caster according to the sensed position of the lever may be turned on. Further, in some embodiments, among the indicators displayed in the respective regions, the indicator(s) except for the turned-on indicator may be turned off.

In some embodiments, the position sensing unit may include plural switches contacting the lever and configured to be turned on according to change of the position of the lever.

In some embodiments, the number of the plural switches may correspond to the number of changeable positions of the lever.

In some embodiments, the position sensing unit may include a photo diode array installed under the lever and configured to sense the position of the lever according to the amount of received light.

In some embodiments, the display unit may be divided into plural regions, and indicators corresponding to respective states of the caster may be printed in the respective regions.

In some embodiments, the indicators printed in the respective regions may be formed of a fluorescent material.

In some embodiments, the caster indicator may further include a connection unit connecting the lever to the display unit and configured to move the position of the display unit according to the moving direction of the lever, and a lid fixed to a link interconnecting levers of casters and covering the upper surface of the display unit, and a display window having a size corresponding to one of the respective regions of the display unit may be formed on the lid.

In some embodiments, the lid may be formed of an opaque material.

In some embodiments, the state of the caster may include at least one of a brake state, a free swivel state and a directional lock state.

One aspect of the present disclosure is a device which includes a caster and any one of the aforementioned caster indicators. In some embodiments, the device may include two casters provided with two levers, respectively, and a link connecting the two levers. In some embodiments of the device, the display unit is attached to the link.

BRIEF DESCRIPTION OF THE DRAWINGS

These and/or other aspects of the present subject matter will become apparent and more readily appreciated from the following description of the embodiments, taken in conjunction with the accompanying drawings of which.

DETAILED DESCRIPTION

Figure 1:
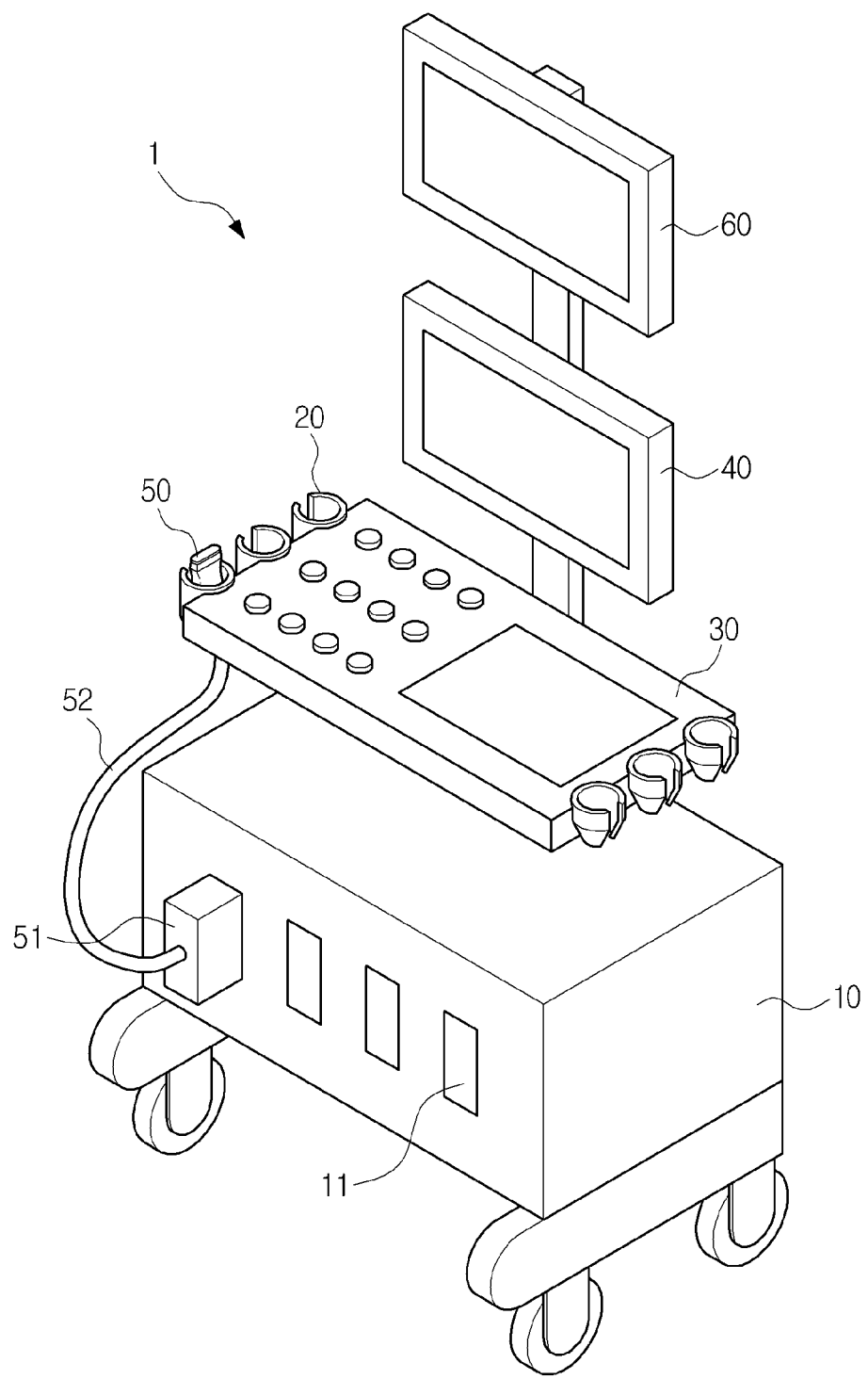
FIG. 1 is an exemplary perspective view illustrating an ultrasonic diagnostic apparatus to which a caster indicator in accordance with one embodiment of the present disclosure is applied.

Reference will now be made in detail to the embodiments of the present disclosure, examples of which are illustrated in the accompanying drawings, wherein like reference numerals refer to like elements throughout. Advantages, features and their achieving methods of the embodiments of the present disclosure will be more clearly understood from the following detailed description taken in conjunction with the accompanying drawings. Although a few embodiments of the present disclosure will be shown and described, it would be appreciated by those skilled in the art that changes may be made in these embodiments without departing from the principles and spirit of the disclosed subject matter, the scope of which is defined in the claims and their equivalents.

Hereinafter, a caster indicator in accordance with one embodiment of the present disclosure will be described with reference to the accompanying drawings. In the drawings, the same or similar elements are denoted by the same reference numerals even though they are depicted in different drawings.

FIG. 1 is an exemplary perspective view illustrating an ultrasonic diagnostic apparatus to which a caster indicator in accordance with one embodiment of the present disclosure is applied.

As shown in FIG. 1, an ultrasonic diagnostic apparatus 1 may include a main body 10, a plurality of probes 50, a control panel 30, a first display device 40, and a second display device 60.

The main body 10 may receive main constituent parts of the ultrasonic diagnostic apparatus 1, for example, a transmission signal generation unit (not shown). If an inspector selects a designated probe 50 from the plural probes 50 provided on the ultrasonic diagnostic apparatus 1, the transmission signal generation unit may generate a transmission signal corresponding to the selected probe 50. Here, the transmission signal may include voltage, burst, and frequency information. A plurality of female connectors 11 may be provided at one side of the main body 10, and a cable 52 connected to the corresponding probe 50 may be connected to each female connector 11. The transmission signal generated by the transmission signal generation unit may be transmitted to the probe 50 via a male connector 51 connected to the female connector 11 of the main body 10 and the cable 52.

The probe 50 contacts the surface of the body of a target object to be inspected, and may transmit and receive ultrasonic waves. In more detail, the probe 50 serves to provide the transmission signal supplied from the main body 10, i.e., ultrasonic waves, to the interior of the body of the target object, to receive an ultrasonic wave signal reflected by a specific region of the interior of the body of the target object, and then to transmit the received ultrasonic wave signal to the main body 10. One end of the cable 52 may be connected to such a probe 50, the male connector 51 may be connected to the other end of the cable 52, and the male connector 51 of the cable 52 may be physically combined with the female connector 11 of the main body 10.

The control panel 30 may be provided with various switches and keys so that an inspector may input instructions required to operate the ultrasonic diagnostic apparatus 1. Here, the various switches and keys may be implemented based on hardware, or be implemented based on software, such as icons of a graphical user interface. Such a control panel 30 may be located above the main body 10.

Probe holders 20 to hang the probes 50 thereon may be provided at the edge of the control panel 30. The probe holders 20 may be provided in number corresponding to the number of the probes 50, and an inspector may hold the probes 50 by hanging the probes 50 on the probe holders 20 at normal times.

The first display device 40 may be located above the control panel 30, and display applications for the plural probes 50. In more detail, the first display device 40 may display a list of the probes 50 connected to the ultrasonic diagnostic apparatus 1. When a list of the probes 50 which are presently connected to the ultrasonic diagnostic apparatus 1 is displayed, the inspector may select a desired probe 50 by operating the switch or the key of the control panel 30. When the inspector selects the probe 50, the first display device 40 may display applications for the selected probe 50. Such a first display device 40 may be a cathode ray tube (CRT) or a liquid crystal display (LCD).

The second display device 60 may be located above the first display device 40, and display a result of ultrasonic diagnosis as an image. In the same manner as the first display device 40, such a second display device 60 may be a cathode ray tube (CRT) or a liquid crystal display (LCD).

A plurality of casters for mobility of the ultrasonic diagnostic apparatus 1 is provided on the lower portion of the main body 10. For example, four casters may be provided. Among these casters, two casters located at the front region of the lower portion of the ultrasonic diagnostic apparatus 1 may be connected by a link. Therefore, the ultrasonic diagnostic apparatus 1 may be fixed to a specific position or moved in a specific direction by changing only one of the two casters.

Hereinafter, the caster indicator in accordance with the embodiment of the present disclosure will be described with reference to FIGS. 2 to 6.

Figure 2:
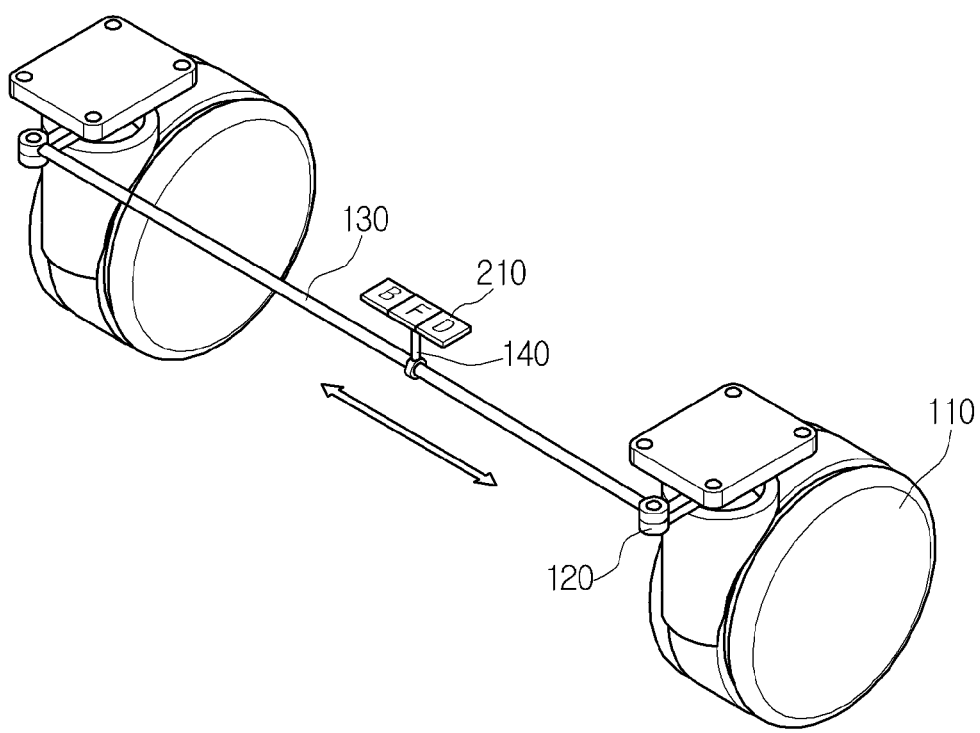
FIG. 2 is an exemplary enlarged perspective view illustrating two casters located at the front region of the ultrasonic diagnostic apparatus shown in FIG. 1.

FIG. 2 is an exemplary perspective view illustrating two casters located at the front region of the ultrasonic diagnostic apparatus shown in FIG. 1.

As shown in FIG. 2, a lever 120 to change the state of the caster 110 protrudes from each of the casters 110, and the lever of the left caster and the lever 120 of the right caster 110 may be connected by a link 130.

FIG. 2 illustrates a case in which the lever 120 is located at the central (neutral) position, and such a lever 120 may move in the direction of an arrow. That is, the lever 120 may horizontally move to left and right from the central position. A user may change the state of the caster 110 by moving the position of the lever 120.

Here, the states of the caster 110 will be described in brief. For example, the caster 110 may have three states, i.e., a brake state, a free swivel state, and a directional lock state. The brake state means a state in which movement of the caster 110 is stopped or the caster 110 is completely locked so as to prevent movement of the caster 110. The free swivel state means a state in which the caster 110 may be rotated under the condition that the caster 110 may freely change direction. The directional lock state (or a swivel lock state) means a state in which the caster 110 may be rotated under the condition that the direction of the caster 110 is fixed.

The state of the caster 110 is changed by moving the position of the lever 120 protruding from the caster 110 to left, the center, or right. The caster 110 may be configured such that the caster 110 is in the free swivel state when the lever 120 is located at the central position. Further, the caster 110 may be configured such that the caster 110 is in the brake state or in the directional lock state when the lever 120 is located at other positions than the central position.

For example, the caster 110 may be configured such that the caster 110 is in the brake state when the lever 120 is located at the left position with respect to the central position, and is in the directional lock state when the lever 120 is located at the right position with respect to the central position.

On the other hand, the caster 110 may be configured such that the caster 110 is in the brake state when the lever 120 is located at the right position with respect to the central position, and is in the directional lock state when the lever 120 is located at the left position with respect to the central position.

Hereinafter, a case in which the caster 110 is in the directional lock state, the free swivel state and the brake state when the caster 110 is located at the left position, the central position and the right position, respectively, will be exemplarily described.

As shown in FIG. 2, since the levers 120 of the respective casters 110 are connected by the link 130, when a user moves one of the two levers 120, the other of the two levers 120 connected to the moving lever 120 may also move.

In more detail, when the user pushes the lever 120 of the right caster 110 to left under the condition that the lever 120 of the right caster 110 is located at the central position, as shown in FIG. 2, the link 130 connected to the lever 120 horizontally moves to left and the lever of the left caster connected to the link 130 moves to left. Consequently, the state of the two casters is changed to the directional lock state.

On the other hand, when the user pushes the lever of the left caster to right under the condition that the lever 120 of the right caster 110 is located at the central position, as shown in FIG. 2, the link 130 connected to the lever horizontally moves to right and the lever 120 of the right caster 110 connected to the link 130 moves to right. Consequently, the state of the two casters is changed to the brake state.

In accordance with the embodiment of the present disclosure, the ultrasonic diagnostic apparatus 1 may be provided with a caster indicator 200 that displays the state of the casters 110.

The caster indicator 200 may include a position sensing unit 220 for sensing the position of the levers 120, a display unit 210 for displaying the state of the casters 110 according to the sensed position of the levers 120, and a power supply unit (not shown) to supply power to the respective constituent elements.

The display unit 210 serves to display the state of the casters 110, and may be installed on the link 130 through a bracket 140. The display unit 210 may include luminous elements, such as light emitting diodes (LEDs), a semiconductor laser, and neon lamps, or be a display element, such as a liquid crystal display (LCD).

As one example, the display unit 210 may be divided into three regions, and indicators corresponding to the states of the casters 110 may be displayed in the respective regions. Here, the indicators may include at least one of figures and letters corresponding to the states of the casters 110. For example, the letters may be names or initials corresponding to the states of the casters 110. In more detail, in case of initials corresponding to the states of the casters 110, an initial 'B' may mean the brake state, an initial 'F' may mean the free swivel state, and an initial 'D' may mean the directional lock state. However, the initials meaning the brake state, the free swivel state and the directional lock state of the casters are not limited to 'B', 'F' and these initials may be replaced with other initials representing the names of the states of the casters.

Further, the names corresponding to the states of the casters may include Korean names, English names including 'Brake', 'Free swivel' and 'Directional lock', and names in other foreign languages. In the respective regions, full names, such as 'Brake', 'Free swivel' and 'Directional lock', may be displayed, or some words of the respective names may be displayed.

According to a result of sensing of the position of the levers 120, an indicator representing the current state of the casters 110 among the letters or figures displayed in the respective regions of the display unit 210 may be turned on, and the remaining indicators unrelated with the current state of the casters 110 may be turned off. Here, the indicators displayed in the respective regions may be turned on in the same color, or be turned on in different colors according to the state of the casters 110. For example, the indicator corresponding to the brake state may be turned on in red, the indicator corresponding to the free swivel state may be turned on in blue, and the indicator corresponding to the directional lock state may be turned on in yellow.

As another example, the display unit 210 may not be divided into plural regions, but may display an indicator representing the current state of the casters 110 according to a result of sensing of the position of the levers 120. For example, if, as a result of sensing of the position of the levers 120, the current state of the casters 110 is the directional lock state, the display unit 210 may display only an indicator corresponding to the directional lock state. Thereafter, when the position of the levers 120 is changed and thus the state of the casters 110 is changed to the free swivel state, the display unit 210 may display only a letter or a figure corresponding to the free swivel state. Here, the letter or the figure displayed through the display unit 210 may be displayed in the same color regardless of the state of the casters 110, or be displayed in different colors according to the state of the casters 110.

Hereinafter, a case in which the display unit 210 is divided into plural regions and initials corresponding to the states of the casters 110 are displayed in the respective regions will be exemplarily described.

The position sensing unit 220 serves to sense the position of the lever 120. Differently from the display unit 210 installed on the link 130 through the bracket 140, the position sensing unit 220 may be installed around at least one of the levers 120 (or both) or at the insides of at least one of the caster 110 (or both) so as to sense the position of the lever 120.

Figure 3:
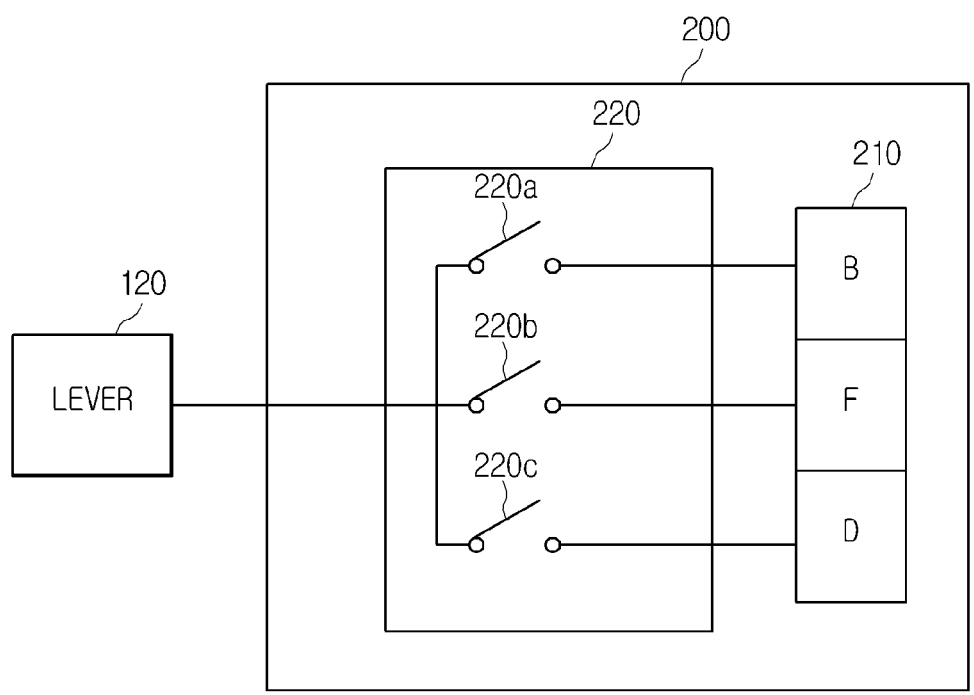
FIG. 3 is an exemplary block diagram illustrating the configuration of the caster indicator in accordance with one embodiment of the present disclosure.

The position sensing unit 220, as shown in FIG. 3, may include a plurality of switches 220a, 220b and 220c. Here, the number of the switches 220a, 220b and 220c may correspond to the number of the changeable positions of the lever 120. That is, since the position of the lever 120 may be changed among three positions, i.e., the left position, the central position and the right position, three switches including a first switch 220a, a second switch 220b and a third switch 220c may be provided. The respective switches 220a, 220b and 220c may be turned on according to the position of the lever 120.

Figure 4:
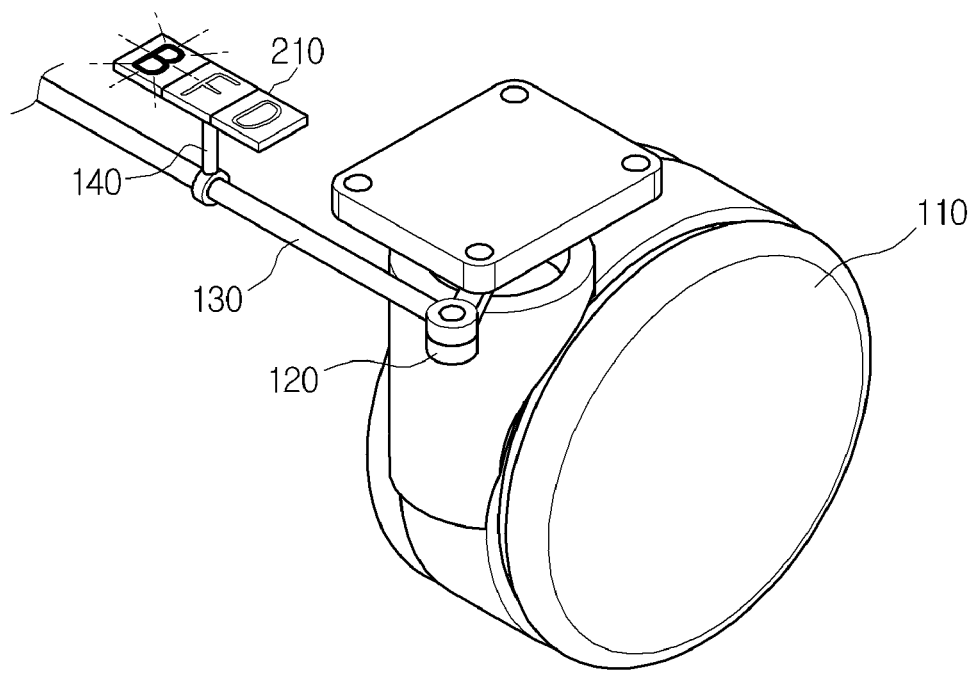
FIG. 4 is an exemplary view illustrating display of the state of a caster, if a lever is located at the right position with respect to the central position.

For example, when a user pushes one end of the lever 120, i.e., a protruding part, to right to locate the end of the lever 120 at the right position, as shown in FIG. 4, the other end of the lever 120 located at the left position. The other end of the lever 120 located at the left position physically contacts the first switch 220a and thus the first switch 220a is turned on, and then the initial 'B' displayed in the region located at the left position among the three regions is turned on. Here, since the remaining initials are turned off, the user may easily confirm that the state of the casters is the brake state.

Figure 5:
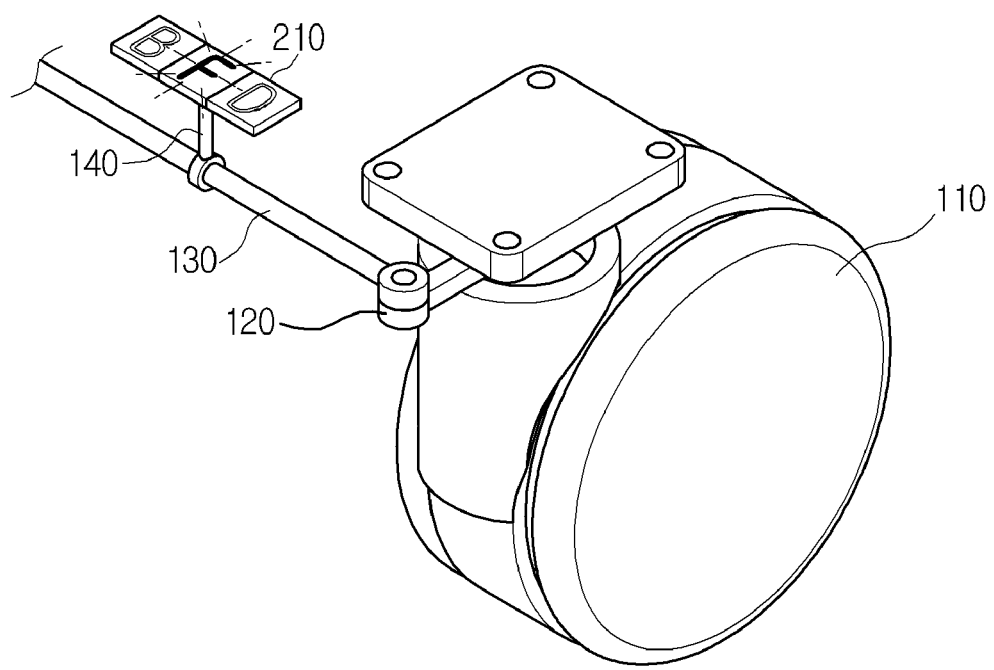
FIG. 5 is an exemplary view illustrating display of the state of the caster, if the lever is located at the center position.

In such a state, when the user pushes the protruding part to the center to locate the protruding part at the central position, as shown in FIG. 5, the other end of the lever 120 is also located at the central position. The other end of the lever 120 located at the central position physically contacts the second switch 220b and thus the second switch 220b is turned on, and then the initial 'F' displayed in the region located at the central position among the three regions is turned on. Here, the on-state of the initial 'B' is changed to the off-state, and the initial 'D' maintains the off-state. Therefore, the user may confirm that the state of the casters is the free swivel state.

Figure 6:
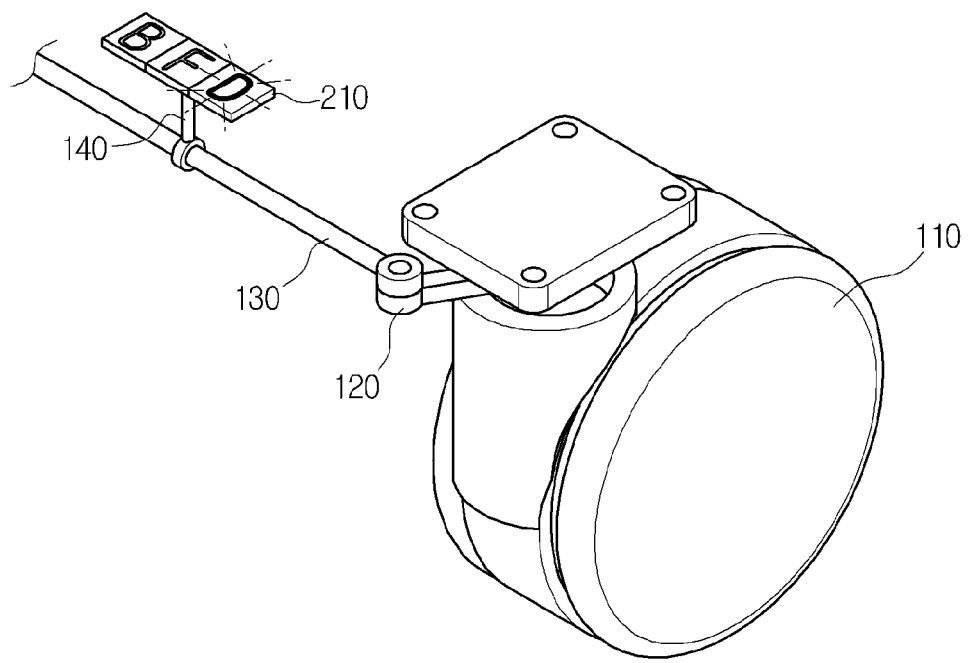
FIG. 6 is an exemplary view illustrating display of the state of the caster, if the lever is located at the left position with respect to the central position.

Thereafter, when the user pushes one end of the lever 120, i.e., the protruding part, to left to locate the end of the lever 120 to the left position, as shown in FIG. 6, the other end of the lever 120 is located at the right position. The other end of the lever 120 located at the right position physically contacts the third switch 220c and thus the third switch 220c is turned on, and then the initial 'D' displayed in the region located at the right position among the three regions is turned on. Here, the on-state of the initial 'F' is changed to the off-state, and the initial 'B' maintains the off-state. Therefore, the user may confirm that the state of the casters is the directional lock state.

The caster indicator 200 in accordance with the embodiment of the present disclosure has been described. This embodiment exemplarily describes the caster indicator 200 in which the position sensing unit 220 includes a plurality of switches 220a, 220b and 220c.

In accordance with another embodiment of the present disclosure, the position sensing unit 220 may include a photo diode array. In more detail, when a photo diode array is installed below the lever 120, an amount of light received by the photo diode array may be varied according to the position of the lever 120. Therefore, the current position of the lever 120 may be judged according to the received amount of light by the photo diode array. For this purpose, in addition to the photo diode array, the caster indicator 200 may further include a controller (not shown), such as a microcomputer.

The caster indicator 200 may further include a transmission unit (not shown). The transmission unit transmits a result of sensing through the position sensing unit 220, i.e., position information of the levers 120, to the main body 10 of the ultrasonic diagnostic apparatus 1. A control device (not shown) provided within the main body 10 may output the state of the casters according to the position information of the levers 120 through one of a visual output method and an auditory output method.

As one example of the visual output method, an icon corresponding to the state of the casters may be displayed through at least one of the first display device 40 and the second display device 60. As another example of the visual output method, a plurality of light emitting elements (not shown) corresponding to the states of the casters may be provided on the control panel 30, and the light emitting element corresponding to the current state of the casters is turned on.

As one example of the auditory output method, a name or an alarm corresponding to the current state of the casters may be output through a sound output device, such as a speaker.

Next, a caster indicator 300 in accordance with another embodiment of the present disclosure will be described. The caster indicator 200 in accordance with the aforementioned embodiment of the present disclosure shown in FIGS. 2 to 6 generates an electrical signal according to the position of the levers 120 through the position sensing unit 220, and displays the state of the casters 110 through the display unit 210 based on the generated signal. Differently from the caster indicator 210 in accordance with the aforementioned embodiment, the caster indicator 300 in accordance with this embodiment of the present disclosure may mechanically connect a display unit 310 to the protruding part of lever 120 using designated connection units, and display the state of caster 110 by changing the position of the display unit 310 according to the position of the lever 120.

In more detail, the caster indicator 300 in accordance with this embodiment may include the display unit 310 on which indicators corresponding to the states of the caster 110 are displayed, a lid 330 fixed to a link 130 and covering the display unit 310, and connection units 340.

The display unit 310 may be divided into plural regions. For example, if the there are three states of the caster 110, i.e., the brake state, the free swivel state and the directional lock state, the display unit 310 may be divided into three regions. Indicators corresponding to the states of the caster 110 are printed in the respective regions. The indicators may include at least one of figures and letters corresponding to the states of the caster 110, and, for example, the letters may be names and initials corresponding to the states of the caster 110. Hereinafter, a case in which an initial 'B' meaning the brake state, an initial 'F' meaning the free swivel state, and an initial 'D' meaning the directional lock state are printed in the respective regions of the display unit 310 will be exemplarily described.

The initials printed in the respective regions of the display unit 310 may be formed of a fluorescent material. The fluorescent material may include a material which fluoresces under visible light, or a material which fluoresces under ultraviolet light.

The connection unit 340 mechanically connects the protruding part of the lever 120 to the display unit 310. Therefore, if the position of the lever 120 is changed, the position of the display unit 310 is changed in the moving direction of the lever 120.

The lid 330 is located above the display unit 310, and may completely cover all of the initials printed in the respective regions. Although not shown in the drawings, the lid 330 may be fixed to a designated position of the link 130 without a bracket 140 (with reference to FIG. 2) or at the circumference of the caster 110. However, the position of the lid 330 is not limited to the circumference of the link 130 or the caster 110, and the lid 330 may be located at any position as long as the lid 330 covers the upper surface of the display unit 310 and is fixed so as not to be influenced by movement of the lever 120. Such a lid 330 may be formed of an opaque material, and a display window 331 having a size corresponding to one of the divided regions of the display unit 310 is provided at the center of the lid 330. The display window 331 may mean an opening from which the lid 330 formed of the opaque material is removed, or mean a region formed of a transparent material differing from other regions of the lid 330 formed of the opaque material.

Figure 7:
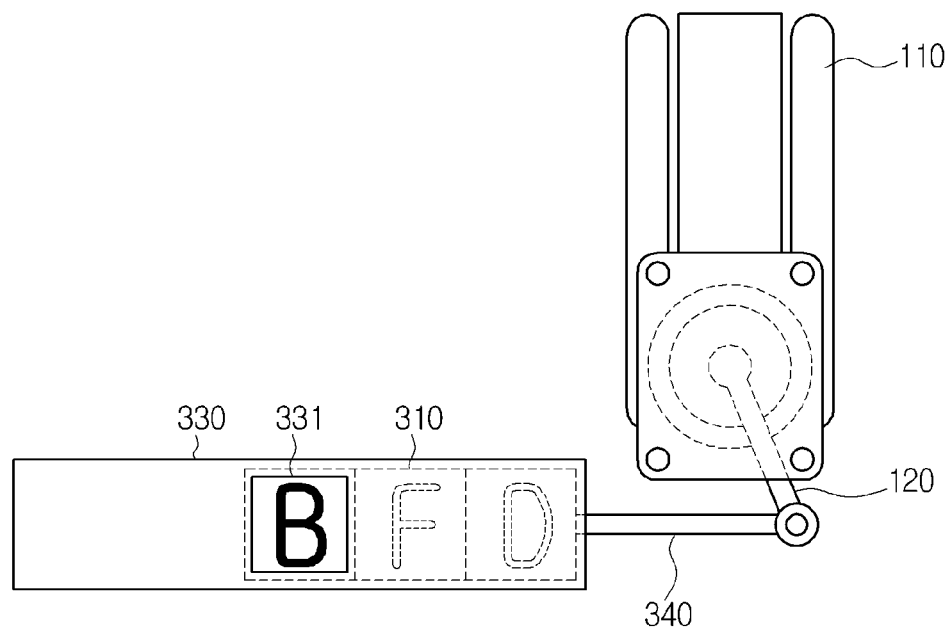
FIGS. 7 to 9 are exemplary views illustrating the states of a caster displayed according to the position of a lever in a caster indicator in accordance with another embodiment of the present disclosure.
Figure 8:
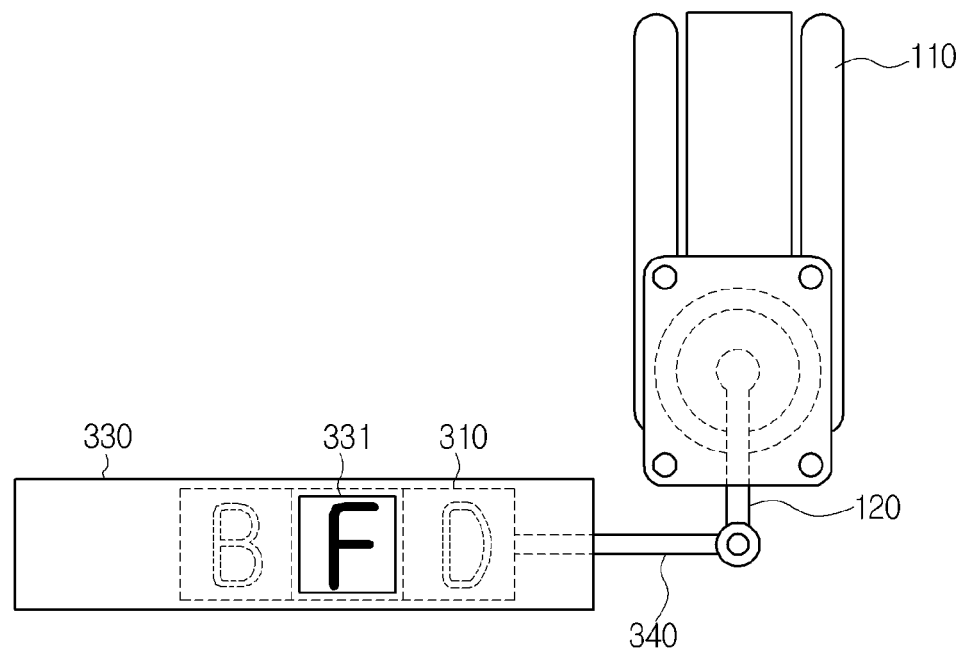
Figure 9:
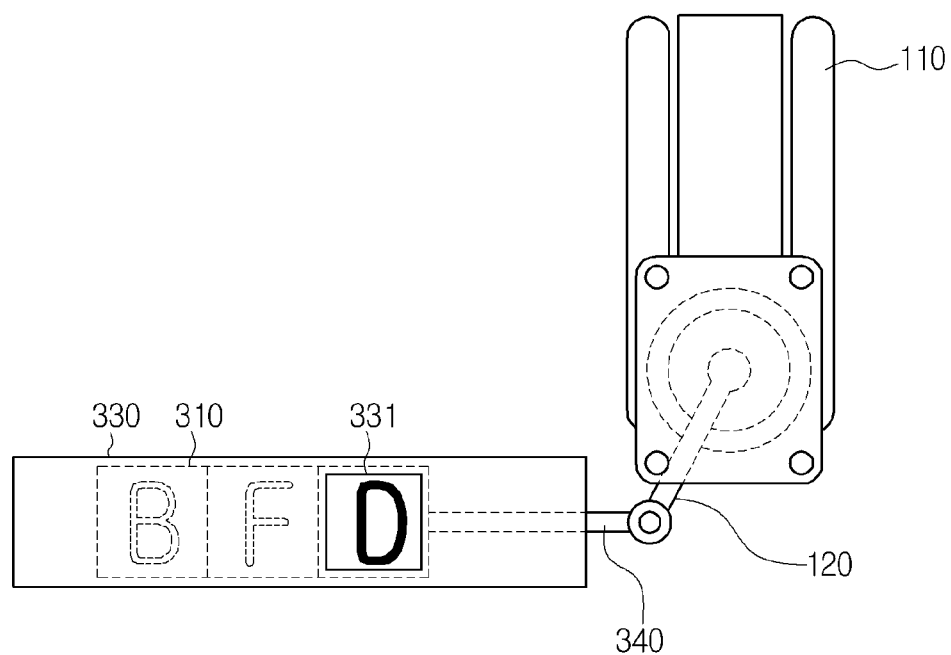

The initial of the display unit 310 located under the lid 330 may be seen through such a display window 331. Since the lid 330 is fixed to the designated position of the link 130 or at the circumference of the caster 110 while the position of the display unit 310 moves in the moving direction of the lever 120, if the protruding part of the lever 120 moves to right, as shown in FIG. 7, the display unit 310 also moves to right in the same manner as the lever 120. Then, the initial 'B' is seen through the display window 331 of the lid 330, and a user may recognize that the current state of the caster 110 is the brake state. In the state of FIG. 7, when the protruding part of the lever 120 moves to left and is thus located at the central position, as shown in FIG. 8, the display unit 310 also moves to left in the same manner as the lever 120. Then, the initial 'F' is seen through the display window 331 of the lid 330, and the user may recognize that the current state of the caster 110 is the free swivel state. In the state of FIG. 8, when the protruding part of the lever 120 moves to left, as shown in FIG. 9, the display unit 310 also moves to left in the same manner as the lever 120. Then, the initial 'D' is seen through the display window 331 of the lid 330, and the user may recognize that the current state of the caster 110 is the directional lock state.

The caster indicator 300 in accordance with this embodiment of the present disclosure has been described.

Although the above-described embodiments exemplarily describe a device and a method in which the state of two casters located at the front region of the ultrasonic diagnostic apparatus is controlled at once and is displayed, embodiments of the present disclosure are not limited thereto but may be applied to a case in which the state of four casters is controlled at once and is displayed as in a medical bed.

As is apparent from the above description, a caster indicator in accordance with one embodiment of the present disclosure has the following effects.

A user may confirm the state of casters through a display unit, and thus unnecessary behavior to confirm the state of the casters is not required.

Even when a medical electronic apparatus is located at a dark place, the user may confirm the state of the casters at a glance.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. A caster indicator comprising:
   plural levers configured to determine states of plural casters, respectively;
   a link configured to connect the plural levers to one another such that positions of the plural levers are simultaneously changed;
   a display unit configured to display the states of the plural casters according to positions of the plural levers, the display unit includes plural regions, and indicators corresponding to respective states of the plural casters are printed in the respective regions;
   a connection unit connecting at least one of the plural levers to the display unit and configured to move a position of the display unit according to a moving direction of at least one of the plural levers; and
   a lid fixed to the link and covering an upper surface of the display unit,
   wherein the lid includes a display window having a size corresponding to one of the respective regions of the display unit.

2. The caster indicator according to claim 1, further comprising a position sensing unit configured to sense the positions of the plural levers.

3. The caster indicator according to claim 2, wherein the display unit is configured to display an indicator corresponding to the states of the plural casters according to the sensed positions of the plural levers.

4. The caster indicator according to claim 2, wherein the display unit displays the indicators corresponding to respective states of the plural casters in the respective regions.

5. The caster indicator according to claim 4, wherein the display unit turns one of the indicators on, which corresponds to the states of the plural casters according to the sensed positions of the plural levers.

6. The caster indicator according to claim 5, wherein the display unit turns one or more indicators except for the one of the indicators off.

7. The caster indicator according to claim 2, wherein the position sensing unit includes plural switches contacting at least one of the plural levers and configured to be turned on according to change of the positions of the plural levers.

8. The caster indicator according to claim 7, wherein a number of the plural switches corresponds to a number of changeable positions of the plural levers.

9. The caster indicator according to claim 2, wherein the position sensing unit includes at least one photo diode array installed under at least one of the plural levers and configured to sense the positions of the plural levers according to an amount of received light.

10. The caster indicator according to claim 1, wherein the indicators printed in the respective regions are formed of a fluorescent material.

11. The caster indicator according to claim 1, wherein the lid is formed of an opaque material.

12. The caster indicator according to claim 1, wherein the states of the plural casters include at least one of a brake state, a free swivel state and a directional lock state.

13. A device comprising:
   plural casters;
   plural levers configured to determine states of the plural casters, respectively;
   a link configured to connect the plural levers to one another such that positions of the plural levers are simultaneously changed;
   a display unit configured to display the states of the plural casters according to positions of the plural levers, the display unit includes plural regions, and indicators corresponding to respective states of the plural casters are printed in the respective regions;
   a connection unit connecting at least one of the plural levers to the display unit and configured to move a position of the display unit according to a moving direction of at least one of the plural levers; and
   a lid fixed to the link and covering an upper surface of the display unit,
   wherein the lid includes a display window having a size corresponding to one of the respective regions of the display unit.

14. The device according to claim 13, wherein the display unit is attached to the link.

15. The caster indicator according to claim 1, wherein the display unit is further configured to display the states such that a movement of the plural levers causes a displayed state to change.

16. The device according to claim 13, wherein the display unit is further configured to display the states such that a movement of the plural levers causes a displayed state to change.

* * * * *